US011052097B2

(12) United States Patent
Tzortzis et al.

(10) Patent No.: US 11,052,097 B2
(45) Date of Patent: Jul. 6, 2021

(54) OLIGOSACCHARIDES COMPOSITION FOR PREVENTING OR REDUCING THE RISK OF METABOLIC SYNDROME

(75) Inventors: Georgios Tzortzis, Berkshire (GB); Jelena Vulevic, Berkshire (GB)

(73) Assignee: Clasado Research Services Limited

( * ) Notice: Subject to any disclaimer, the term of this patent is extended or adjusted under 35 U.S.C. 154(b) by 197 days.

(21) Appl. No.: 14/130,883

(22) PCT Filed: Jun. 20, 2012

(86) PCT No.: PCT/GB2012/051418
§ 371 (c)(1),
(2), (4) Date: Jan. 3, 2014

(87) PCT Pub. No.: WO2013/005001
PCT Pub. Date: Jan. 10, 2013

(65) Prior Publication Data
US 2014/0142061 A1  May 22, 2014

(30) Foreign Application Priority Data
Jul. 5, 2011 (GB) ........................................ 1111452

(51) Int. Cl.
*A61K 31/702* (2006.01)
*A61K 31/7016* (2006.01)
*A61P 31/06* (2006.01)

(52) U.S. Cl.
CPC ........ *A61K 31/702* (2013.01); *A61K 31/7016* (2013.01); *A61P 31/06* (2018.01)

(58) Field of Classification Search
CPC .............. A61K 31/702; A61K 31/7016; A61K 2300/00
USPC ......... 514/54, 61, 53, 23; 536/123.1, 123.13
See application file for complete search history.

(56) References Cited

U.S. PATENT DOCUMENTS

| 6,368,591 B1 * | 4/2002 | Chen ....................... C12R 1/225 424/93.4 |
| 2010/0069327 A1 * | 3/2010 | Van De Heijning ... A23L 33/40 514/58 |

FOREIGN PATENT DOCUMENTS

| CA | 2 725 039 | | 1/2010 | |
| JP | 62-210965 | | 9/1987 | |
| JP | 2-109964 | | 4/1990 | |
| JP | 2003-339348 | * | 12/2003 | ........... A61K 31/702 |
| JP | 2003339348 | A | 12/2003 | |
| JP | 2010-6718 | | 1/2010 | |
| JP | 2010-6718 | A | 1/2010 | |
| WO | WO 2005/003329 | A1 | 1/2005 | |
| WO | WO2010/003803 | * | 1/2010 | ........... A61K 31/702 |
| WO | WO 2010/023422 | | 3/2010 | |
| WO | WO2010/023422 | A1 | 3/2010 | |

OTHER PUBLICATIONS

Cholongitas et al. (Scandinavian Journal of Gastroenterology, 2008; 43: 1405-1406).*
Merriam-Webster's Third New International Dictionary, Dec. 2000.*
Lim et al. (J. Vet. Sci. (2004), 5(4), 391-395).*
Totani et al. (Kobe Medical Journal, vol. 205, No. 4, 2003. 4. 26, pp. 273-274; English Translation).*
Torres et al., "Galacto-Oligosaccharides: Production, Properties, Applications, and Significance as Prebiotics" Comprehensive Reviews in Food Science and Food Safety vol. 9 pp. 438-454 (Year: 2010).*
Chonan et al., "Effect of Galactooligosaccharides on Calcium Absorption and Preventing Bone Loss in Ovariectomized Rats" Bioscience, Biotechnology, and Biochemistry vol. 59 No. 2 pp. 236-239 (Year: 1995).*
English machine translation of JP2003-339348 above, downloaded from worldwide.espacenet.com (Year: 2003).*
Van Aeeuwen et al., "Comparative structural characterization of 7 commercial galacto-oligosaccharide (GOS) products" Carbohydrate Research vol. 425 pp. 48-58 (Year: 2016).*
International Search Report and Written Opinion for PCT/GB2012/051418 dated Aug. 2, 2012, 12 pages.
Depeint, et al., Prebiotic evaluation of a novel galactooligosaccharide mixture produced by the enzymatic activity of *Bifidobacterium bifidum* NCIMB 41171, in healthy humans: a randomized, double-blind, crossover, placebo-controlled intervention study, The American Journal of Clinical Nutrition, American Society for Nutrition, vol. 87, No. 3, XP008115815, ISSN 0002-9165, Mar. 1, 2008, pp. 785-791.
Martin, et al., Top-down systems biology integration of conditional prebiotic modulated transgenomic interactions in a humanized microbiome mouse model, Molecular Systems Biology, vol. 4, XP002680209, ISSN: 1744-4292, pp. 1-17, 2008.
Vulevic, et al., Modulation of the fecal microflora profile and immune function by a novel trans-galactooligosaccharide mixture (B-GOS) in healthy elderly volunteers, The American Journal of Clinical Nutrition, American Society for Nutrition, vol. 88, No. 5, XP008117002, ISSN: 0002-9165, Nov. 1, 2008, pp. 1438-1446.
Clinical Trials.gov; "Efficacy of a Prebiotic Galactooligosaccharide to reduce metabolic syndrome risk factors in overweight adults"; Oct. 2009; 3pp.
Xiaoyun, Han et al.; "Intestinal microbes and chronic diseases"; Chinese Journal of Microecology; vol. 21; No. 11; Nov. 2009; 15pp. (English translation).
Jia, Jian-ping et al.; "Advance in the research of galactooligosaccharides"; China Dairy Industry; vol. 31; No. 1; 2003; 9pp. (English translation).
Zhao, Liping et al.; "Dynamics and functional analysis of gut microbiota in obesity and metabolic diseases"; Chinese Bulletin of Life Sciences; vol. 22; No. 12; Dec. 2010; 19pp. (English translation).
Delzenne, Nathalie M. et al.; "Prebiotics and lipid metabolism" Curr. Opin. Lipidol; 13(1); 2002; pp. 61-67.

(Continued)

*Primary Examiner* — Eric Olson
(74) *Attorney, Agent, or Firm* — Lewis Roca Rothgerber Christie LLP

(57) ABSTRACT

The present invention relates to the use of a galactooligosaccharide composition for preventing or reducing the risk of developing metabolic syndrome.

5 Claims, No Drawings

(56) References Cited

OTHER PUBLICATIONS

Neyrinck, Audrey M. et al.; "Prebiotic Effects of Wheat Arabinoxylan Related to the Increase in Bifidobacteria, Roseburia and Bacteroides/Prevotella in Diet-Induced Obese Mice"; PLOS One; vol. 6; Issue 6; Jun. 2011; 12pp.

MacFarlane, G.T. et al.; "Bacterial metabolism and health-related effects of galacto-oligosaccharides and other prebiotics"; Journal of Applied Microbiology; ISSN 1364-5072; 2007; 40pp.

Depeint, F., et al., Prebiotic evaluation of a novel galactooligosaccharide mixture produced by the enzymatic activity of Bifidobacterium bifidum NCIMB 41171, in healthy humans: a randomized, double-blind, crossover, placebo-controlled intervention study, Am J Clin Nutr, 2008, 87, pp. 785-791.

\* cited by examiner

OLIGOSACCHARIDES COMPOSITION FOR PREVENTING OR REDUCING THE RISK OF METABOLIC SYNDROME

CROSS-REFERENCE TO RELATED APPLICATION(S)

This is a National Phase Patent Application and claims priority to and the benefit of International Application No. PCT/GB2012/051418, filed on Jun. 20, 2012, which claims priority to and the benefit of British Patent Application No. 1111452.7, filed on Jul. 5, 2011, the disclosures of which are hereby incorporated by reference in their entireties.

The present invention relates to a composition comprising a mixture of galactooligosaccharides for use in a method for the prevention or reduction of the risk of developing metabolic syndrome. It also relates to a method of preventing or reducing the risk of developing metabolic syndrome by orally administering a composition comprising a mixture of galactooligosaccharides. Galactooligosaccharides are non-digestible carbohydrates which are resistant to mammalian gastrointestinal digestive enzymes but are fermented by specific colonic bacteria.

Metabolic syndrome is the name given to a group of risk factors that occur together and that result in an increase in the risk of cardiovascular disorders such as coronary artery disease, heart disease, heart attack and heart damage, as well as increased risk of stroke.

There have been several definitions of metabolic syndrome but the most commonly used one at present is the World Health Organisation (WHO) definition.

According to WHO the criteria or risk factors for metabolic syndrome are 1) central obesity with a waist:hip ratio above 0.9 for men and 0.85 for women; 2) body mass index (BMI) above 30 kg/m$^2$; 3) blood pressure above 140/90; 4) triglycerides above 1.7 mmol/l; 5) high density lipoprotein (HDL) cholesterol <0.9 mmol/l in men and <1 mmol/l in women; 6) glucose fasting or 2 hours after a glucose load above 7.8 mmol/l and 7) glucose uptake during hyperinsulinaemic euglycaemic clamp in lowest quartile for population.

In general, an individual's risk of heart disease, diabetes and stroke increases with the number of metabolic risk factors they have. A person who has metabolic syndrome is twice as likely to develop heart disease and five times as likely to develop diabetes as someone who does not have metabolic syndrome.

To date, the goal of managing metabolic syndrome is to reduce the risk of heart disease and diabetes. Doctors usually recommend lifestyle changes and/or prescribe medicines, such as a combination of beta-blockers, diuretics and/or a daily low-dose of aspirin to reduce blood pressure, low density lipoprotein (LDL) cholesterol and blood sugar. Recommendations for lifestyle changes will include weight loss, probably by eating 500-1,000 fewer calories per day, and 30 minutes of moderate intensity exercise, such as walking, 5-7 days per week.

It has now been found in a double-blind randomised, placebo controlled, cross-over human trial that oral administration of a composition comprising a mixture of galactooligosaccharides can lower cholesterol and triglyceride levels in the blood and thus be used in a method for the prevention or reduction of the risk of developing metabolic syndrome.

The mixture of galactooligosaccharides comprised disaccharides Gal (β1-3)-Glc; Gal (β1-3)-Gal; Gale (β1-6)-Gal; Gal (α1-6)-Gal; trisaccharides Gal (β1-6)-Gal (β1-4)-Glc; Gal (β1-3)-Gal (β1-4)-Glc; tetrasaccharide Gal (β1-6)-Gal (β1-6)-Gal (β1-4)-Glc and pentasacharide Gal (β1-6)-Gal (β1-6)-Gal (β1-6)-Gal (β1-4)-Glc.

This mixture of galactooligosaccharides is disclosed in EP 1 644 482, which describes a novel strain of *Bifidobacterium bifidum* that produces a galactosidase enzyme activity that converts lactose to this novel mixture of galactooligosaccharides. This novel mixture has been shown to have prebiotic and anti-inflammatory properties in the gut.

This mixture of galactooligosaccharides is marketed commercially under the name Bimuno (registered trade m ark) and is available from Clasado Ltd (Milton Keynes, UK).

According to one aspect of the invention there is provided a composition comprising a mixture of galactooligosaccharides as defined above for use in a method for preventing or reducing the risk of developing metabolic syndrome.

This mixture of galactooligosaccharides may also be used in a method for the prevention of cardiovascular disorders such as coronary artery disease, coronary heart disease, heart attack and stroke. An effective amount of galactooligosaccharide is preferably administered daily as a single dose or alternatively as two separate doses several hours apart.

According to a second aspect of the invention there is provided a method of preventing or reducing the risk of developing metabolic syndrome comprising administering to a mammal such as a human an effective amount of a galactooligosaccharide composition comprising a mixture of galactooligosaccharides as defined above.

The product known as Bimuno comprises at least 49% of the dry matter as the mixture of galactooligosaccharides. The remainder of the composition may comprise non-active components such as glucose, galactose, lactose, acacia gum and citric acid.

The composition may be presented in freeze-dried powder form, in syrup form or in pastille form. It is preferably taken orally on a daily basis. The powder composition preferably comprises from 1.35 g to 9.6 g of galactooligosaccharide in 2.75 g to 20 g of the powdered composition, preferably from 1.96 g to 4.9 g of galactooligosaccharide in 4 g to 10 g of the powder, most preferably 2.7 g galactooligosaccharide in 5.5 g of composition. The composition may be added to a drink, preferably a hot drink, or sprinkled on food, for example, on breakfast cereal.

Alternatively, the galactooligosaccharide may be presented as a syrup or pastilles (dehydrated syrup) in which the non-active components may comprise glucose, galactose, lactose and citric acid. A daily dose of the syrup may comprise from 1.35 g to 9.6 g of the galactooligosaccharide mixture in 3.55 g to 25.29 g of the syrup composition, preferably from 1.96 g to 4.9 g of galactooligosaccharide in 5.16 g to 12.9 g of the syrup, most preferably 2.7 g galactooligosacchride in 7.25 g of the syrup.

The invention will be further described by way of reference to the following examples:—

EXAMPLE 1

Freeze-dried powdered composition packaged in a 'stick-pack' and containing per 5.5 g final product:

| | |
|---|---|
| Galactooligosaccharide (GOS) mixture | 2.75 g |
| Lactose | 1.40 g |
| Monosaccharides (glucose, galactose) | 0.64 g |
| Drying aid | 0.24 g |
| Ash | 0.23 g |
| Moisture | 0.19 g |
| Protein | 0.05 g |

EXAMPLE 2

Syrup composition per 7.25 g finished product:

| | |
|---|---|
| Galactooligosaccharide (GOS) mixture | 2.75 g |
| Lactose | 0.58 g |
| Monosaccharides (glucose, galactose) | 1.69 g |
| Ash | 0.23 g |
| Moisture | 1.95 g |
| Protein | 0.05 g |

EXAMPLE 3

Effectiveness of galactooligosaccharides on metabolic syndrome risk factors in overweight adults Study A total of 45-50 human subjects with three or more risk factors associated with metabolic syndrome and its increased risk of cardiovascular disease were recruited. Equal numbers of men and women were included in the study cohort.

Metabolic syndrome factors used to select subjects included: insulin resistance (measured as increased ratio of fasting glucose (6-7 mmol/l) and insulin), high blood pressure, dyslipidaemia [low high density lipoprotein (HDL) cholesterol (<1 mmol/l), high triglyceride (>1.3 mmol/l)], waist circumference (>40 in men; >35 in women).

Further inclusion criteria were:—
- 18-65 years
- BMI >25 kg/m$^2$
- not having suffered a myocardial infarction/stroke or cancer in the past 12 months
- not diabetic (diagnosed or fasting glucose >7 mmol/l) or suffering from other endocrine disorders
- not suffering from chronic coronary, renal, bowel disease/gastrointestinal disorder or having a history of choleostatic liver or pancreatitis
- not on drug treatment for hyperlipidaemia, hypertension, inflammation, hypercoagulation or using drugs that affect intestinal motility or absorption
- no history of alcohol/drug abuse
- not planning or on a weight reducing regime
- not taking any dietary antioxidant or other phytochemical, prebiotics or probiotic supplements
- not pregnant, lactating, planning a pregnancy in the next 6 month or of child bearing potential and not using effective contraceptive precautions
- not taking antibiotics for the previous 1 month
- not anaemic (haemoglobin men >14 g/dl; women >11.5 g/dl)
- non smokers Volunteers who met the inclusion criteria were asked to attend a screening session during which a fasting (12 hours) blood sample was taken and their BMI, waist circumference and blood pressure measured. The screening blood sample (~10 ml) was analysed at the Royal Berkshire Hospital for total cholesterol (TC), HDL cholesterol, triacylglycerol, glucose and insulin. Individuals who were anaemic (Hb<14 g/dl male, 11.5 g/dl female) or who had 'abnormal' blood biochemistry based on the above analysis, were automatically excluded. The measurements were used to identify individuals at higher metabolic risk, who were then invited to participate in the study.

Treatment A or B was randomly assigned to each participant using an allocation ratio of 1:1 for the 2 study groups (including stratification for gender). Volunteers were required to attend the University for a total of 6 visits. The study was a randomised, controlled, double-blind crossover trial with Maltodextrin as the placebo. Volunteers were instructed to ingest the test product (GOS) and/or placebo daily for 12 weeks, with a 6 week washout period between. Both GOS and placebo were supplied in powder sachets (5.5 g) and volunteers were instructed to either sprinkle these over a bowl of cereal or add them to any drink, and ingest them daily. Habitual diet was assessed by pre-validated 4-day food diaries (2 weekend and 2 week days). At 0, 6 and 12 wk of intervention, volunteers visited the nutrition unit and samples and measurements were taken.

On each visit a fasting blood sample (~20 ml) as taken and this was used to analyse a number of risk markers (all using commercially available kits). The markers studied were:

Lipid profile (total, low density lipoprotein (LDL) and HDL cholesterol, triglycerides and non-esterified fatty acids)

Insulin resistance derived from fasted measures of glucose and insulin ratio

Inflammatory/thrombotic biomarkers (including C-reactive protein, and IL6)

At 0, 12, 18 and 30 weeks a series of anthropometric measurements (including weight, blood pressure and waist circumference) were taken in order to determine any changes.

Results

Baseline Characteristics of Subjects

The demographic characteristics of the study population are presented in Table 1.

TABLE 1

Baseline characteristics of subjects participating in the study.

| Characteristics | Male (n = 16) | Female (n = 29) |
|---|---|---|
| Age (yr) | 42.8 ± 12.1 | 46.4 ± 11.8 |
| BMI (kg/m$^2$) | 30.7 ± 5.3 | 32.1 ± 6.3 |
| Waist circumference (cm) | 103.7 ± 11.0 | 99.2 ± 14.5 |
| Fasting insulin (pmol/L) | 66.3 ± 28.3 | 70.3 ± 30.6 |
| Fasting glucose (mmol/L) | 5.5 ± 0.8 | 5.2 ± 0.6 |
| Systolic Blood Pressure (mmHg) | 127.9 ± 10.1 | 125.9 ± 15.8 |
| Diastolic Blood Pressure (mmHg) | 80.9 ± 8.6 | 80.5 ± 10.0 |
| Total Cholesterol (mmol/L) | 6.3 ± 1.5 | 6.2 ± 1.2 |
| HDL cholesterol (mmol/L) | 1.3 ± 0.4 | 1.4 ± 0.3 |
| TAG (mmol/L) | 1.9 ± 0.9 | 1.4 ± 0.5 |

Effect on Colonic Microbiota

Daily consumption of 5.5 g of Bimuno (2.75 g active GOS) showed after 6 wk to result in a significant increase in the bifidobacterial population compared to both the Placebo (1 wk) (p<0.05) and baseline (p<0.05) levels (Table 2). After 12 wk of consumption, Bimuno intake resulted in significant increase in the populations of *Bifidobacterium* and *Lactobacillus* spp compared to Placebo (12 wk) (p<0.0001) and baseline (p<0.05). At the same time the levels of species of the *Clostridium hystoliticum* group and *Desulfovibrio* spp were significantly reduced compared to Placebo (12 wk) (p<0.0001) and baseline (p<0.05) (Table 2).

In terms of changes in the populations of *Atopobium* spp, *C. coccoides/E. rectale*, *E. cylindroides*, *E. hallii*, *Clostridium* cluster IX, *F. prausnitzii* cluster, beta-Proteobacteria, *Bacteroides* spp no significant effect was recorded either after the intake of Bimuno or Placebo during the 12 wks treatment period.

Effect on Biomarkers of Inflammation

Results on the levels of faecal sIgA (secretory immunoglobulin A), faecal calprotectin and blood inflammatory biomarkers (IL-6, CRP) during the study periods (Placebo, Bimuno) are shown in Table 3.

Daily intake of Bimuno for 12 weeks resulted in a significant reduction of both secretory IgA ($p<0.05$ vs Placebo; $p<0.01$ vs baseline) and calprotectin ($p<0.01$ vs placebo; $p<0.05$ vs baseline) (Table 3). At the same time a significant reaction in the blood levels of the pro-inflammatory cytokine IL-6 ($p<0.05$ vs Placebo; $p<0.05$ vs baseline) and in the inflammatory biomarker C-reactive protein ($p<0.05$ vs Placebo; $p<0.05$ vs baseline) was determined after daily intake of Bimuno for 12 weeks.

Effect on Metabolic Syndrome Risk Factors

Daily intake of Bimuno for 12 weeks resulted in a significant reduction in blood insulin levels ($p<0.05$ vs Placebo; $p<0.01$ vs baseline), blood triglycerides ($p<0.05$ vs placebo; $p<0.05$ vs baseline), total cholesterol ($p<0.05$ vs Placebo; $p<0.05$ vs baseline) and the ratio of total cholesterol over HDL cholesterol ($p<0.05$ vs Placebo; $p<0.05$ vs baseline) indicating an overall reduction of the risk of Metabolic syndrome (Table 4).

CONCLUSION

Supplementation with 5.5 g Bimuno (delivering 2.75 g of active GOS) in a population at risk of developing metabolic syndrome resulted in a significant change in the composition of their colonic microbiota by increasing the resident beneficial bacteria of *Bifidobacterium* genus and *Lactobacillus* genus, while decreasing the levels of detrimental bacteria such as those belonging to the *C. hystoliticum* subgroup and the sulphate reducing bacteria. This microbiota change resulted in an increase in the colonisation resistance in the gut reducing the colonic inflammation as seen through the reduction of the calprotectin levels. At the same time increased levels of sIgA would suggest a better barrier function of the epithelium which in combination with the reduced colonic inflammation could result in the reduction of the levels of inflammatory biomarkers in the host (IL-6, CRP).

This overall protection through the improvements in the composition of the colonic microbiota and the intestinal barrier function appears to have a beneficial effect in the levels of insulin, cholesterol and triglycerides that are known risk factors of metabolic syndrome.

TABLE 2

Changes in the numbers ($Log_{10}$) of the various bacterial groups monitored during the study periods (Placebo, Bimuno), as determined by fluorescent in situ hybridisation (FISH)

|  | Placebo | | 5.5 g Bimuno | |
| --- | --- | --- | --- | --- |
|  | Wk6 | Wk12 | Wk6 | Wk12 |
| *Bifidobacterium* spp | 0.17 ± 0.13 | 0.3 ± 0.19 | 0.78 ± 0.23* | 1.13 ± 0.29* |
| *Lactobacillus-Enterococcus* spp | −0.04 ± 0.09 | −0.12 ± 0.18 | 0.24 ± 0.15 | 0.43 ± 0.22* |
| *C. hystoliticum* group | 0.15 ± 0.11 | 0.23 ± 0.07 | 0.12 ± 0.21 | −0.61 ± 0.24* |
| *Desulfovibrio* spp | 0.02 ± 0.09 | −0.03 ± 0.11 | −0.04 ± 0.07 | −0.63 ± 0.17* |

*significantly different from Baseline ($p < 0.05$)

TABLE 3

Changes in the levels of the faecal and blood biomarkers of inflammation during the study periods (Placebo, Bimuno)

|  | Placebo | | 5.5 g Bimuno | |
| --- | --- | --- | --- | --- |
|  | Wk6 | Wk12 | Wk6 | Wk12 |
| sIgA (ug/g faeces) | NA | −230 ± 243 | NA | 902 ± 214* |
| Calprotectin (ug/g faeces) | 2.57 ± 4.03 | 2.58 ± 3.28 | −2.91 ± 3.97 | −9.61 ± 3.27* |
| IL-6 (ng/ml) | NA | 7.97 ± 13.01 | NA | −33.34 ± 12.9* |
| C-Reactive protein (ng/ml) | 0.46 ± 0.42 | 0.75 ± 0.40 | 0.66 ± 0.39 | −1.56 ± 0.41* |

*significantly different from Baseline ($p < 0.05$)

TABLE 4

Changes in the levels of insulin, TAG and cholesterol after 12 wk supplementation of Placebo or Bimuno

|  | Placebo | | 5.5 g Bimuno | |
| --- | --- | --- | --- | --- |
|  | Wk6 | Wk12 | Wk6 | Wk12 |
| Insulin (pmol/L) | 5.15 ± 3.14 | 7.42 ± 2.89 | −0.02 ± 0.07 | −10.37 ± 3.04* |
| Triglycerides (mmol/L) | 0.09 ± 0.08 | −0.03 ± 0.09 | −0.08 ± 0.09 | −0.79 ± 0.11* |
| Total Cholesterol (mmol/L) | 0.14 ± 0.11 | 0.05 ± 0.06 | −0.10 ± 0.08 | −0.39 ± 0.12* |
| Total Cholesterol:HDL | 0.01 ± 0.04 | −0.06 ± 0.09 | −0.19 ± 0.08 | −0.44 ± 0.1* |

*significantly different from Baseline ($p < 0.05$)

The invention claimed is:

1. A method for lowering levels of total cholesterol, triglycerides, and/or non-esterified fatty acids in a human, the method comprising administering to a human with elevated levels of total cholesterol, triglycerides, and/or non-esterified fatty acids an effective amount of a galactooligosaccharide composition comprising a mixture of galactooligosaccharides comprising disaccharides Gal ($\beta$1-3)-Glc; Gal ($\beta$1-3)-Gal; Gal ($\beta$1-6)-Gal; Gal ($\alpha$1-6)-Gal; trisaccharides Gal ($\beta$1-6)-Gal ($\beta$1-4)-Glc; Gal ($\beta$1-3)-Gal ($\beta$1-4)-Glc; tetrasaccharide Gal ($\beta$1-6)-Gal ($\beta$1-6)-Gal ($\beta$1-4)-Glc and pentasacharide Gal ($\beta$1-6)-Gal ($\beta$1-6)-Gal ($\beta$1-6)-Gal ($\beta$1-4)-Glc;
    wherein the galactooligosaccharide composition is administered without a probiotic strain.

2. The method according to claim 1 wherein the composition is in the form of a freeze-dried powder, a syrup, or a pastille.

3. The method according to claim 1 wherein the galactooligosaccharide composition is administered orally on a daily basis as a single dose or two separate doses.

4. The method according to claim 2 wherein the composition is in the form of a freeze-dried powder composition, comprising from 1.35 g to 9.6 g of galactooligosaccharides in 2.75 g to 20 g of the freeze-dried powder composition.

5. The method according to claim 2 wherein the composition is in the form of a syrup composition, comprising from 1.35 g to 9.6 g of galactooligosaccharides in 3.55 g to 25.29 g of the syrup composition.

* * * * *